United States Patent [19]

Stierman et al.

[11] Patent Number: 4,912,228

[45] Date of Patent: Mar. 27, 1990

[54] PROCESS OF EXTRACTION OF AMINO ACIDS FROM AQUEOUS SOLUTIONS THEREOF

[75] Inventors: Thomas J. Stierman; Phillip L. Mattison, both of Santa Rosa, Calif.

[73] Assignee: Henkel Research Corporation, Santa Rosa, Calif.

[21] Appl. No.: 228,357

[22] Filed: Aug. 4, 1988

[51] Int. Cl.⁴ .................. C07D 233/64; C07C 101/22; C07C 101/08

[52] U.S. Cl. ..................................... 548/344; 548/497; 562/443; 562/445; 562/559; 562/560; 562/562; 562/570; 562/571; 562/573; 562/575; 562/576

[58] Field of Search ............... 548/344, 497; 562/560, 562/575, 562, 559, 576, 443, 570, 445, 573, 571

[56] References Cited

U.S. PATENT DOCUMENTS

| | | | |
|---|---|---|---|
| 3,966,594 | 6/1976 | Ohkawa et al. | 210/638 |
| 4,275,234 | 6/1981 | Baniel et al. | 562/580 X |
| 4,584,399 | 4/1986 | Portal et al. | 562/443 |
| 4,661,606 | 4/1987 | Tuominen et al. | 548/497 |

FOREIGN PATENT DOCUMENTS 0073381 3/1983 European Pat. Off. .

Primary Examiner—Richard A. Schwartz
Attorney, Agent, or Firm—Ernest G. Szoke; Wayne C. Jaeschke; Patrick J. Span

[57] ABSTRACT

An improvement in the process of extraction of amino acids from aqueous solutions in which the amino acids are extracted with quaternary ammonium extractants. A pretreatment of the amino acid containing aqueous solution with a tertiary amine prior to extraction of the amino acids with the quaternary ammonium extractant, removes some impurities or poisons present therein, leaving the amino acids in the aqueous solution for subsequent extraction with a water insoluble quaternary ammonium extractant. After extraction with the quaternary extractant, the organic phase is stripped of amino acid and the stripped organic is subjected to an acidic scrub before returning to the quaternary extraction stage.

22 Claims, 1 Drawing Sheet

PROCESS OF EXTRACTION OF AMINO ACIDS FROM AQUEOUS SOLUTIONS THEREOF

BACKGROUND OF THE INVENTION

1. Field of the Invention:

This invention relates to improvement in the process of extraction of amino acids from aqueous solutions in which the amino acids are extracted with quaternary ammonium extrantant. In particular the invention relates to treatment to remove poisons which interfere with the overall extraction process and recovery of amino acid. Such poison removal treatment involves a pretreatment of the amino acid containing aqueous solution prior to extraction of the amino acid with the quaternary ammonium extractant and an acidic scrub treatment subsequent to the quaternary extraction to remove any remaining poisons. The pretreatment comprises an extraction of the aqueous solution with a tertiary amine to remove some of the impurities or poisons present along with the amino acids in the aqueous solution. The pretreatment extraction is carried out in a water immiscible organic solvent. This pretreatment removes the impurities leaving the amino acids in the aqueous solution for subsequent extraction with a water insoluble quaternary ammonium extractant. After extraction with the quaternary extractant, the organic phase is stripped of the amino acid and the stripped organic is subjected to an acidic scrub before being returned to the quaternary extractant stage.

2. Description of the Related Art

Extraction of amino acids using quaternary ammonium extractants can be seen from U.S. Pat. No. 4,661,606. As described therein amino acids are essential to animal and human nutrition and thus the production and purification of amino acids is an important procedure. Due to present industrial procedures it is necessary to remove amino acids from dilute fermentation broths and various aqueous mixtures. U.S. Pat. No. 4,661,606 describes a method by which the amino acids can be extracted from such dilute fermentation broths using water insoluble quaternary ammonium extractants dissolved in a water immiscible organic solvent. The amino acids are extracted from the aqueous phase into the organic phase, and due to the immiscibility of the two phases, these can be separated and the amino acids subsequently recovered from the organic phase (see FIG. 1). However, in the aqueous solutions containing the amino acids, there are other components present which interfere by complexing irreversibly with the extractant.

In co-pending U.S. application Ser. No. 864,064 filed May 16, 1986 a number of improvements in the process are described which involve various possible pretreatments of the fermentation broth before extraction with the quaternary ammonium extractant. Such pretreatments include ultrafiltration and/or an adsorption treatment. The ultrafiltration is useful in removing cellular materials present and other materials as described. The adsorption treatment utilizes materials such as clay or clay like materials, activated carbon and lime.

Another patent relating to purification of phenylalanine is U.S. Pat. No. 4,584,399. This patent discloses treatment of the phenylalanine containing aqueous solution, by ultrafiltration or centrifuging, to remove cellular material, contacting the filtered solution with an ion exchanger, such as a strongly acidic microporous resin, to absorb the phenylalanine, and eluting the absorbed phenylalanine.

While not related to recovery of amino acids South African Patent Application No. 84-6024 by Hoeschst Aktiengesellschaft relates to isolation of enzymatically produced carboxylic acids such as lactic acid and citric acid using an anion exchanger, i.e. polymer containing tertiary amino groups. The carboxylic acids are absorbed by the polymer containing the tertiary amino groups and then desorbed therefrom by treatment with a polar solvent from the group of aliphatic alcohols, ketones or carboxylic acid esters. Similarly U.S. patent 4,275,234 relates to a process for recovery of acids such as citric acid, lactic acid, oxalic and phosphoric acids from aqueous solutions by extraction with secondary or tertiary amines in a water immiscible organic solvent. The organic extract is then subjected to a stripping operation in which the acid is stripped from the organic into an aqueous stripping solution and the aqueous acid containing phase separated from the organic extractant phase.

Other patents and articles dealing with treatments of amino acids and materials or treatments related to this invention are:

| U.S. Pat. Nos. | | |
| --- | --- | --- |
| 3267029 | 3412018 | 3966594 |
| 4523999 | 4663048 | 3318867 |
| 4137405 | 4168268 | 3944606 |
| 4275234 | 4372923 | 3320024 |
| 4379126 | 4162230 | 3215622 |

Publications (1) "Transport of Amino Acids through Organic Liquid Membranes"; Behr and Lehn, J. Am. Chem. Soc., 95, 6108–6110, (9173).

(2) "Reactive Extraction of Salicyclic Acid and d,1-Phenylalanine in a Stirred Cell"; Schlichting, Halwachs, and Shugerl; Chem. Eng. Comm., vol. 51, pp. 193–205 (1987).

(3) "Reactive Extraction of d, 1-Phenylalanine with TrioctylMethyl-Ammonium Chloride (TOMAC) As a Carrier" Haensel, Halwachs and Schugerl, Chem. Engr. Sc., Vol. 41, No. 7, pp. 1811–1815, (1986).

(4) Reaktivextraktion von Salicylsaeure und d,1-Phenylalanin" Halwachs, Schlichting and Schugerl, Chem. Ind. (Dusseldorf), 36, 458 (1984).

(5) "Quantitative Determinations by Ion Pair Extractions", Nordgren and Modin, Acta. Pharm. Swec., 12, pp. 407–416, (1975).

(6) "Principles of Ion-Pair Extraction", Cox, Chemistry and Industry, 16 May 1981, pp. 355–358.

(7) "Extraction of Organic Acids by Ion-Pair Formation with Trin-oxtylamine", Puttemans, Dryon and Massact, Analytica Chimica Acta, 161, pp. 221–229, (1984).

(8) "Extraction Chemistry of Fermentation Product Carboxylic Acids", Kertes and King, Biotechnology and Bioengineering, 28, pp. 269–282, (1986).

(9) "Extraction of Citric Acid from Fermentation Broth Using a Solution of a Tertiary Amine", Wennersten, J. Chem. Tech. Biotechnol, 33B, pp. 85–94 (1983).

(10) "A New Method for the Purification of Citric Acid by LiquidLiquid Extraction", Wennersten, ISEC 80, 2, pp. 1, 3, 5, 7 (1980).
(11) "Study on Extraction of Citrid Acid", Yu-Ming et al, ISEC 83, p. 517 (1983).
(12) "Acid Extraction By Amines", Siebenhoffer and Marv, ISEC 83, p. 517 (1983).
(13) Chemical Abstracts, CA 104: 231525, "Effect of the Nature of a Solvent on Anion Exchange Extraction of Amino Acids", (1986).

JAPANESE PATENTS (1) JP 83-57158 (KoKoKu No. 59-23797; KoKai No. 53-99396)
(2) JP 84-23797 (KoKoKu No. 57-57158; KoKai No. 53-34989)

BRIEF DESCRIPTION OF THE INVENTION

It has now been found that while the pretreatments of ultrafiltration or with adsorbents described in the copending application noted above, provide desirable advantages in the process, some drawbacks remain. In the extraction of amino acids, particularly the extraction of phenylalanine (PHE) from commercial fermentation broths using quaternary ammonium extractant as described in the aforementioned U.S. Pat. No. 4,661,606 a number of components other than the amino acid may be extracted. Some of these are extracted to only a slight degree and are removed in subsequent stages and accordingly do not interfere significantly with the over-all recovery process. However, some of these components are extracted and do not strip off under the recovery process conditions and these accumulate in the organic quarternary ammonium phase thereby taking up an increasing share of the loading sites, leading to "poisoning" of the organic reagent. If not countered in some way, the ability to extract the amino acid is lost and the organic phase must be replaced usually at substantial cost. The present invention minimizes or reduces the poisoning problem. This solution involves the use of an extraction pretreatment which utilizes a tertiary amine extractant, hereinafter specified, which extracts the various impurity components without extracting the amino acids. The tertiary amine is water-insoluble and is dissolved in a water immiscible organic solvent. Because of immiscibility, two separate phases form which can be separated. The tertiary amine-organic phase contains the extracted impurities while the amino acids remain in the aqueous phase. The aqueous phase containing the amino acids are then extracted using a water insoluble quaternary ammonium extractant, hereinafter specified, dissolved in a water immiscible organic solvent. Upon separation of the two phases the amino acids can then be recovered from the organic phase in the usual manner and the quaternary ammonium extractant organic phase recycled for re-use. The tertiary amine organic phase containing the impurities or "poisons" can also be treated to strip out the impurities leaving the tertiary amine extractant organic phase for recycle and re-use.

By use of the present invention significant reduction of the rate of poisoning of the quaternary ammonium reagent is achieved, up to about 90% reduction being typical. The process of the present invention can be briefly summarized (see FIG. 2) as a process for the extraction of amino acids from an aqueous solution containing at least one of the amino acids comprising:

(a) contacting the aqueous solution with a solution of a water-insoluble tertiary amine extractant in a water-immiscible organic solvent forming two phases, an organic phase (I) containing organic impurities originally present in the aqueous solution along with the amino acids therein and an aqueous phase (II) in which the amino acids are retained;

(b) separating the immiscible organic phase (I) from the aqueous phase (II).

(c) contacting the aqueous phase (II) adjusted to alkaline pH with a water-insoluble quaternary ammonium extractant in a water-immiscible organic solvent wherein the amino acids are extracted from the aqueous phase (II) into the quaternary ammonium organic phase (III);

(d) separating the immiscible organic phase (III) from the amino acid barren aqueous phase (IV); and (e) recovering the amino acid from said organic phase (III); and where any remaining impurities are present;

(f) scrubbing said organic phase (III), now barren of amino acid, with an acidic scrub solution prior to return or reuse of the organic phase for further extraction.

The amino acids are recovered or removed from the quaternary ammonium organic phase generally by stripping therefrom by treatment or contact of the organic phase with an aqueous acidic solution followed by subsequent recovery of the amino acid from the aqueous acidic strip solution by conventional methods of precipitation, crystallization or the like. Alternatively, by appropriate selection of conditions, the amino acids may be precipitated as they are stripped or otherwise removed from the organic phase.

DETAILED DESCRIPTION AND PREFERRED EMBODIMENTS

Figure 1:
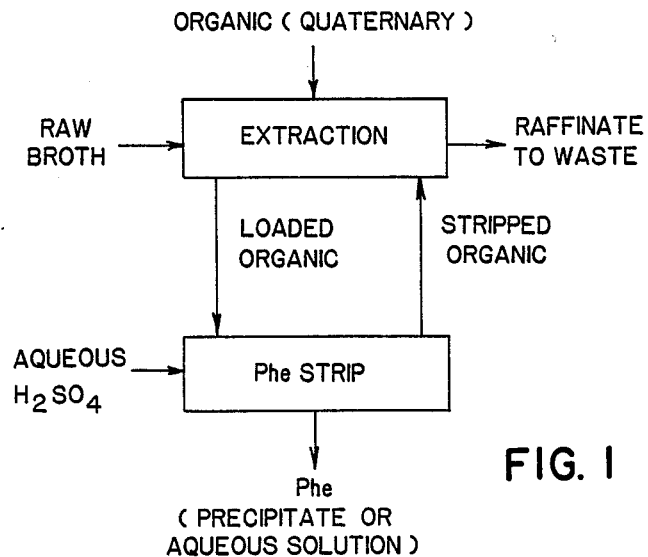
FIG. 1 is a block diagram representation of the process of U.S. Pat. No. 4,661,606, as referred to in the Discussion of Related Art above.
Figure 2:
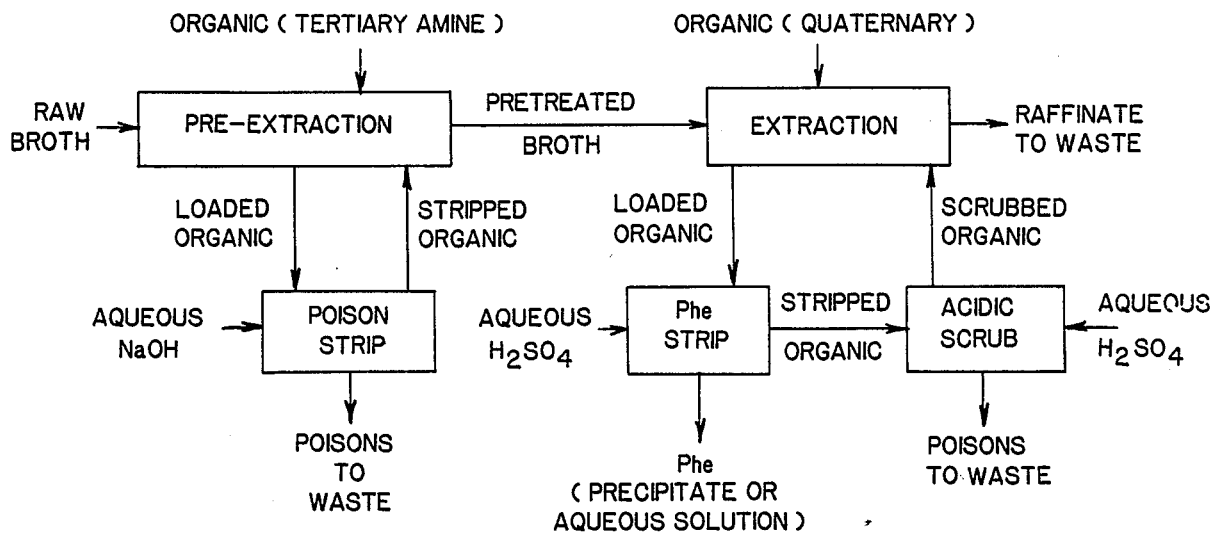
FIG. 2 is a block diagram representation of the process of the present invention, as referred to above in the BRIEF DESCRIPTION OF THE INVENTION.

The amino acids to which the present invention is applicable are arginine, histidine, isoleucine, leucine, lysine, -methionine, phenylalanine, threonine, tryptophan, $\beta$-alanine, tyrosine, glutamic acid and aspartic acid. The amino acid of particular significant is phenylalanine, hereinafter also referred to as "PHE". Also of particular significance is tryptophan, hereinafter referred to as "TRP".

The amino acids to which this invention relates, can also be defined as an organic acid containing an amino group. Most naturally occurring acids in this category are alpha-amino acids having the $NH_2$ group attached to the carbon atom next to the COOH group; beta-alanine being a naturally occurring amino acid not following this rule.

The water-insoluble extractants employed in this invention to draw or extract amino acids into organic solutions from aqueous solutions containing the amino acid are quaternary ammonium compounds having a total of at least 16, and preferably 25 carbon atoms, preferably those having a quaternary ammonium ion of the formula:

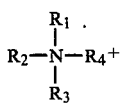

where $R_1$, $R_2$, $R_3$ and $R_4$ individually are aliphatic hydrocarbon groups containing from about 1 to about 22 carbon atoms and where $R_1$, $R_2$, $R_3$ and $R_4$ together have a minimum of at least 16, and preferably, 25 carbon atoms, and where at least three of the four R groups have at least 4 carbon atoms.

As indicated the amino acids are recovered from aqueous solutions, generally fermentation broths obtained from the fermentation production of amino acids. Illustrative broths are noted in the copending U.S. Application Serial No. 864,064 filed May 16, 1986, the disclosure of which is hereby incorporated by reference. EP Publication No. 73381 is one reference noted illustrating useful fermentation broths. The present invention is particularly useful for the processing of phenylalanine, lysine or tryptophan fermentation broths. Generally such broths have already had cellular materials substantially removed by conventional filtration or other methods although some cellular material and undesirable impurities may be present, such as various organic carboxylic acids other than the desired amino acids. The fermentation broths to which the invention is particularly applicable are those containing at least one of the desired amino acids in typical concentration about 1% to about 5%.

In the extraction of amino acids from commercial fermentation broths using quaternary ammonium extractants, particularly the recovery of phenylalanine, PHE, it was found that the recovery of PHE decreases over time or recycle of the organic extraction solution. This was the result of loading capacity loss in the quaternary organic extraction solution due to extracted impurities which did not strip from the organic under the normal conditions of the process. The irreversibly extracted impurities are referred to as "poisons" as they accumulate in the organic phase taking up a share of the loading sites, leading to "poisoning" of the quarternary organic reagent. The observed poisoning of the quarternary ammonium organic extraction solution can lead to significantly increased processing costs as the organic phase must be replaced to maintain the ability to extract the amino acid.

The invention consists of process improvements useful for prevention of provisioning of the quaternary ammonium organic extractant solution. The first improvement comprises a pretreatment extraction of the fermentation broth to remove "poisons" prior to the amino acid extraction with the organic quaternary ammonium extractant solution. This pretreatment is a pre-extraction using a water-immiscible organic solution of a tertiary amine containing at least 18, and preferably, 20 carbon atoms.

The tertiary amine organic solution serves to extract organophilic acid impurities or "poisons". These acid impurities can generally be described as organophilic acids which are aliphatic, aromatic or araliphatic, either unsubstituted hydrocarbon chains or hydroxy substituted hydrocarbon chain acids. Such compounds may contribute to the poisoning problem. Other unidentified fermentation products, such as phospholipids, may also be "poisons" and be extracted by the tertiary amine extraction solution.

The tertiary amines useful in the pretreatment extraction may be generally described as water-insoluble tertiary amines containing aliphatic, araliphatic or aromatic hydrocarbon groups and having at least 18, and preferably, 20 carbon atoms. Amines having less than 20 carbon atoms tend to be less soluble in the organic solvent or diluent in which they are dissolved to form the organic extractant phase, and tend to be too soluble in the aqueous phase from which the acid impurities are to be extracted.

The preferred tertiary amines may be ideally defined by the formula

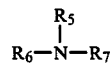

where $R_5$, $R_6$ and $R_7$ individually are alphatic, araliphatic or aromatic hydrocarbong groups containing from 1-22 carbon atoms with the total number of carbon atoms in groups $R_5$, $R_6$ and $R_7$ being at least 18, and preferably, 20. Groups which are aliphatic hydrocarbon groups are preferred with those containing at least 8 carbon atoms being more desirable. High purity ion-pair extractants commercially available from Henkel Corporation are: ALAMINE ® 300 (tri-n-octylamine), ALAMINE 308 (tri-isoctylamine), ALAMINE 336 (tri($C_8C_{10}$) amine), ALAMINE 310 (tri-isodecylamine) and ALAMINE 304 (tri-laurylamine). Of these, the ALAMINE 336 is preferred for use in the present invention.

As indicated, the tertiary amine is dissolved in a waterimmiscible organic solvent which solution comprises the organic extractant phase into which the impurities leading to poisoning are extracted from the aqueous broth. Any substantially water immiscible liquid solvent can be used for solution of the tertiary amine. The same water-immiscible solvents are used for the quaternary-ammonium extractant organic solution in subsequent extraction of the amino acids. Typically the solvents are the aliphatic and aromatic hydrocarbons. Aliphatic hydrocarbons such as alkanes, including cycloalkanes and halogenated alkanes are suitable. Preferred alkanes have a minimum of five carbon atoms. Preferred halogenated alkanes have a minimum of two carbon atoms. Aromatic hydrocarbons which can be used include benzene, and substituted products such as toluenes, xylenes and cumene. Also suitable as solvents are those esters, ethers, ketones, and alcohols which are substantially water immiscible. Furthermore, any blend of these substances or a water immiscible kerosene is also suitable. Preferred organic solvents are the aliphatic hydrocarbon having flash points of 150° F., and higher and solubilities in water of less than 0.1% by weight. These solvents are also essentially non-toxic and chemically inert and the costs thereof are currently within practical range. Representative commercially available solvents are: Kermac 470B (an aliphatic kerosene available from Kerr-McGee, Flash Point, 175° F.); Chevron Ion Exchange Solvent (available from Standard Oil of California; Flash Point, 195° F.); Escaid 100 and 110 (available from Exxon-Europe, Flash Point, 180° F.); Exxsol D80, available from Exxon USA corresponds to Escaid 110; Norpar 12 (available from Exxon-U.S.A., Flash Point, 160° F.); Conoco C-1214L (available from Conoco, Flash Point, 160° F.); Aromatic 150 (an aromatic kerosene available from Exxon-U.S.A., Flash Point 150° F.) and various other kerosenes and petroleum fractions from other oil companies.

Modifiers can be added to the solvent in addition to the extractant in order to modify or improve the extraction of amino acids. Substances, which are preferred as modifiers are alcohols in the range of from about 10 to about 13 carbon atoms and phenols such as the alkyl (8-12 carbon atom) substituted phenols, which can be used to improve amino acid extraction, phase separation and/or other important characteristics of the organic solution. When typically employed in the tertiary amine extraction, the modifier, such as tridecanol will be employed in amounts up to the amount by weight of the tertiary amine in the organic solution.

In the pretreatment extraction with tertiary amine it is preferred that the pH of the broth be adjusted to a pH below 6 and preferably in the range of about 2-3.5. Under these conditions, the acid impurities will be extracted from the aqueous solution or broth while the amino acids will remain in the aqueous solution. In this extraction, as well as in the subsequent extractions of amino acids with a quaternary ammonium compound, the extraction process is preferably conducted in a countercurrent continuous process, but may be conducted in a batch process. Also, acid or base is added to the aqueous solution to adjust the pH to the level desired. Suitable acids to be used for pH control in the aqueous mixture are mineral acids. If any adjustment is required with base, the suitable bases are the alkali metal and alkaline earth metal hydroxides and ammonium hydroxide. The stronger acids or bases which tend to be soluble in water and insoluble in the organic phase are preferred. Such acids are hydrochloric, hydrofluoric, nitric, sulfuric, hydrobromic and phosphoric. Sulfuric acid is a preferred acidifying agent for the aqueous phase. Suitable bases for pH control in the aqueous phase, particularly for adjustment to alkaline pH for the extraction with the quaternary, include alkali metal or alkaline earth metal bases, particularly potassium hydroxide, sodium hydroxide, ammonium hydroxide and sodium carbonate.

The concentration of the tertiary amine extractant in the organic phase should be sufficient to extract the poisoning impurities from the aqueous phase. Generally an extractant concentration to acid impurities concentration is on a 1:1 molar basis. Preferably the concentration of tertiary amine to acid impurity should be from about 1.2 moles. It is generally not required to employ above 2.5 moles but larger amounts can be employed if desired.

Two phases are formed in the extraction which are immiscible and which can be separated. Prior to being recycled and returned to the circuit for extraction the organic phase containing the tertiary amine and extracted impurities, is stripped of the impurities by a basic stripping phase. Suitable bases for the stripping or wash are the alkali metal or alkaline earth metal bases such as those noted earlier and ammonium hydroxide. A caustic, NaOH, wash is preferred. After stripping of the impurities the tertiary amine organic phase is returned to the circuit for re-use.

In order to extract the amino acids from the aqueous solution thereof using the quaternary solution ammonium extractant (after pretreatment extraction with the tertiary amine to remove the impurities), the pH of the aqueous solution is controlled or adjusted so that the amino acids are not present as zwitterion. The zwitterion is that form of an amino acid where the amino acid molecule contains both a positive and negative charge. This form, which will vary slightly with the specific amino acid in solution, occurs in an aqueous solution over the more neutral pH ranges (from about 4.5 to 7.5). To extract amino acids with the quaternary extractant therefore requires the aqueous mixture containing amino acids to have an alkaline or a basic pH value above 7.5, preferably above 10 or 11. When water insoluble quaternary ammonium salts are used as the extractant in the organic phase, the aqueous phase will generally have a pH of 12 or 12.5 or greater, for preferred operation of the invention.

The concentration of the extractant used in the organic phase should be sufficient to extract a portion of the amino acids from the aqueous phase. Where a variety of amino acids are present, it is possible to limit the concentration of the extractant so that the extractant to amino acid molar concentration ratio is from about 0.25:1 to about 1.35:1. This will enable amounts of the more hydrophobic amino acid to extract and separate from the more hydrophilic amino acids.

Extractions of several amino acids simultaneously from fermentation broths and other aqueous mixtures can also be accomplished using the instant invention. In this instance an overall and substantially complete removal of amino acids from the aqueous mixture is desired. Acceptably, the ratio of extractant concentration to amino acid concentration is 1:1 on a molar basis. Preferably the ratio should be from about 1.2 moles of extractant per amino acid molar concentration, to about 10 moles of extractant per total moles of amino acid. As previously indicated, however, the concentration of extractant can be limited to less than 1 mole per mole of amino acids in order to extract more preferentially one amino acid over another. Thus, the ratio of the number of moles of extractant in the organic solution to the number of moles of amino acids in the aqueous solution can acceptably be in the range of from about 0.25 moles of extractant per mole of amino acid to about 10 moles of extractant per mole of amino acid.

In the extraction process of the instant invention the respective concentrations of the organic and aqueous phases can vary widely depending on individual circumstances and needs. The process of the instant invention operates well with very dilute solutions. Again the extraction process is preferably conducted in a countercurrent continuous process, but may be conducted in a batch process.

There is no upper limit to the amount of amino acids in the aqueous phase. In fact solid or precipitated amino acids can also be in contact with the aqueous phase to permit continued replenishment of the amino acid concentration. There is no minimum concentration necessary for the amino acids in the aqueous solution. One advantage of the instant invention is that extractions can be done with very dilute solutions, in which amino acids frequently are found. For extremely dilute amino acid solutions, extractant concentrations and the organic to aqueous phase ratio can be varied to improve extraction. A solution having any detectable amount of amino acids can be extracted. The instant invention can be used to extract amino acids from solutions with amino acid concentrations as low as 10 ppm (parts per million).

The respective volumes of the phases in both the tertiary amine extractions and the amino acid extraction with the quaternary are generally determined by individual need, such as the type of extraction system used, and the respective concentrations of the solutions. Since amino acids must frequently be extracted from very dilute aqueous solutions, the organic to aqueous volume ratio can acceptably vary from about 1:20 to about 20;1. More desirably, a more effective range for the ratio of the organic phase volume to the aqueous phase volume is from about 1:5 (organic to aqueous) to about 5:1 (organic to aqueous). A more preferred ratio for the organic phase volume to the aqueous phase volume, especially in commercial extraction systems is from about 1:3 to about 3:1.

The organic extractant phase should contact the aqueous amino acid phase for a sufficient length of time to permit entry of the extracted material into the organic phase. The time of contact depends on the particular system, the type of equipment used, and upon individual needs and desires. As a general rule, however, the contact time between the organic extractant solution and the aqueous solution should be in excess of 0.1 seconds with some equipment, but generally less than 3 hours. Naturally a minimum contact time is desired, thus a more desirable phase contact time would be in the range of from about 5 seconds to one hour while a more preferred contact time is from about 5 seconds to about 10 minutes.

After the amino acids have been extracted into the organic phase, the two phases may be separated by any convenient means for a liquid/liquid phase separation. Representative but nonexhaustive examples of means for achieving phase separations are: gravity settlers and centrifuges. Generally, any system used to separate different liquid phases can be used.

After the amino acids have been extracted into the organic phase they can be further purified and isolated. Separation of the amino acids from the extractants will free the extractants for re-use in which more amino acids are extracted from other aqueous mixtures. As disclosed in the copending U.S. Application Serial No. 864064, noted earlier, the removal of the amino acid from the organic solution may be carried out in any four different variations described below:

(a) contacting the organic solution containing the amino acid with a concentrated acid solution, such as 85% sulfuric acid, in an amount to precipitate the amino acid, in the absence of any aqueous phase;

(b) contacting the organic solution containing the amino acid with an aqueous acidic solution saturated with the amino acid whereby the amino acid precipitates being insoluble in the organic and the aqueous phases:

(c) contacting the organic solution containing the amino acid with an aqueous acidic solution, whereby the amino acid is transferred to the aqueous acidic phase, which is separated from the organic phase, and precipitating the amino acid from the aqueous phase by adjusting the temperature or the pH level so as to precipitate the amino acid;

(d) contacting the organic solution containing the amino acid with a brine at a pH greater than or equal to that at the isoelectric point whereby the amino acid is displaced from the extraction in the organic solution and transferred to the aqueous solution.

In variation (a) above, the amino acid is precipitated from the organic extractant solution containing the amino acid by contacting the water immiscible organic solution with a concentrated acid solution in an amount sufficient to precipitate the amino acid. Concentrated solutions of acids, such as sulfuric acid, phosphoric acid, hydrohalide such as hydrochloric or hydrobromic, tetrafluoroboric, hexafluorophosphoric and nitric are representative of those which are employed. Sulfuric acid is preferred. The stripping of the PHE from the quaternary organic phase is generally conducted at an equilibrium pH between 3 and 7, preferably 4 to 5.5.

In variation (b), the same acids noted in (a) may be employed. In this variation, three phases are present:
(1) the organic phase
(2) the aqueous phase saturated with the amino acid; and
(3) a solid amino acid phase.

The solid phase may be removed by filtration or centrifugation leaving the two immiscible organic and aqueous phases, which can be separated and recycled for use in the circuit.

In variation (c), the amino acids are released from the extractant and transferred into an aqueous acid stripping solution.

After the amino acid is removed or stripped from the loaded organic phase, the stripped organic phase is scrubbed or washed before return to the extraction stage to remove any remaining impurities (poisons). If little poisons remain, the stripped organic phase can merely be returned to the extraction stage without scrubbing; however, since as a practical matter, there will be at least some small amount of impurities remaining, only a portion of the stripped organic phase is subjected to the post-extraction acidic scrub. When the amino acid is removed from the quaternary ammonium organic phase by precipitation therefrom, using 85% $H_2SO_4$, no aqueous phase is formed and the amino acid barren, organic phase is subsequently washed, after removal of the precipitated amino acid, with the aqueous acidic scrub solution. If after stripping, the barren organic phase retains a residual amount of amino acid, the organic phase may be washed with water to ensure complete removal of amino acid prior to washing with the aqueous acidic scrub solution. When the amino acid is removed from the quaternary ammonium organic phase by use of an aqueous acidic solution, such as an aqueous sulfuric acid solution, the sulfuric acid must be employed in an amount stoichiometric to the amino acid present in the organic phase to avoid removal of the impurities along with the amino acid. The organic phase, then barren of the amino acid but containing the remaining impurities, is washed with the aqueous acidic scrub solution. Aqueous sulfuric acid solutions are the preferred acidic scrub solutions. The scrubbing is preferably conducted at an equilibrium pH of less than about 3, with an equilibrium pH of between 1 and 2 being preferred.

The following examples serve to illustrate, but not limit, the invention. All parts and percentages are by weight, unless otherwise noted. In the examples, the fermentation broth used was a phenylalanine, PHE, broth typically containing about 1 to 3% of the amino acid. Otherwise, chemicals were as follows:

ALIQUAT 336: methyltri($C_8$-$C_{10}$)ammonium chloride available from Henkel Corporation.

ALAMINE 336: tri($C_8$-$C_{10}$)amine available from Henkel Corporation.

EXXSOL D80: low aromatic kerosene available from Exxon (also available as Escaid 110).

Tridecyl alcohol: available from Exxon.

In the examples, the quaternary ammonium sulfate organic extraction solution was prepared by dissolving ALIQUAT 336 (135 g/l) and tridecyl alcohol (150 g/l)

in low aromatic kerosene and washing the resulting solution with several one volume portions of aqueous sodium sulfate (100 g/l).

EXAMPLE A

This example is a control to illustrate the analytical technique used to monitor the "poison" content of a fermentation broth and to provide a comparison to the ideal behavior of a synthetic broth containing no "poisons".

The level of "poisons" present in a fermentation broth is quantified by the observed reduction in loading capacity of an organic extraction solution which has been contacted with the fermentation broth. The following procedure was used to measure this loss of loading capacity:

"Poison" Quantification

The fermentation broth of interest is first adjusted with caustic (50% aqueous sodium hydroxide) to a pH of 11-12 and diluted to 14-15 g/l PHE. This fermentation broth (10 parts) is contacted with quaternary amine organic extraction solution (1 part) by shaking for 30 min. The aqueous and organic phases are separated. The recovered "poison" loaded organic phase (1 part) is then contacted two times with a synthetic PHE broth (10 parts, 15 g/l PHE, pH 11-12) for 30 min each, using a fresh portion of synthetic broth for the second contact. These synthetic PHE broth washes of the organic solution serve to remove components of the broth which are reversible extracted (and therefore not "poisons") and to load the organic solution with the maximum amount of PHE that is can accommodate. The resulting organic solution is finally analyzed for PHE concentration. This concentration is the loading capacity of the organic solution resulting after extraction of the "poisons" present in the broth being tested.

The "poison" quantification, as just described, was conducted on a synthetic PHE broth (15.0 g/l PHE, pH 12.0) to determine the loading capacity of the organic extraction solution in the absence of any "poisons". Similarly, a sample of diluted and pH adjusted PHE fermentation broth (13.9 g/l PHE, pH 11.7) was also examined. The synthetic broth resulted in a PHE loading capacity of 33.7 g/l PHE, while the fermentation broth gave an organic with a loading capacity reduced to 18.8 g/l. The difference between the loading capacity observed for the synthetic broth and that for the fermentation broth reflects the quantity of "poisons" present in the fermentation broth. Thus, the "poisons" present in the fermentation broth resulted in a loss of loading capacity of 14.9 g/l PHE.

EXAMPLE 1

A sample of the same fermentation broth used in Example A (1 part, 13.9 g/l PHE, pH 11.7) was acidified with 85% sulfuric acid to a pH of 3.0 and filtered to remove precipitated material. This pH 3 broth was contacted three times with a tertiary amine organic pretreatment solution (1 part, 120 g/l ALAMINE 336, 150 g/l tridecyl alcohol, in EXXSOL D80) for 30 min each, using a fresh portion of the organic solution for each contact. The pH of the pretreated broth was then adjusted back to a pH of 12.0 with 50% sodium hydroxide and filtered. The resulting broth was analyzed and found to contain 14.0 g/l PHE, indicating that no measurable PHE loss occurred by the described pretreatment.

The "poison" content of this ALAMINE 336 pretreated broth was measured, by the procedure described in Example A, and found to result in an organic loading capacity of 28.6 g/l PHE. Thus, the loss of loading capacity for this broth was reduced to ca. 15% from the 44% loss observed for this broth without the described pretreatment. This equates to a 66% reduction in poisoning.

EXAMPLE 2

A sample of another PHE fermentation broth was acidified with 85% sulfuric acid, filtered, and diluted. The resulting broth (1 part, 13.8 g/l PHE, pH 1.46) was contacted with a tertiary amine organic pretreatment solution (1 part, 15 wt % ALAMINE 336, 18.7 wt % tridecyl alcohol, in EXXSOL D80) by continuous countercurrent extraction using a 2" diameter Karr column. The recovered pretreated broth had a pH of 3-4. This broth was then adjusted to pH 12 with 50% sodium hydroxide and enough PHE was added to result in a PHE concentration of 14-15 g/l. The "poison" content of the resulting broth was determined, by the procedure described in Example A, and found to result in a loading capacity of 31.0 g/l PHE. The "poison" content of the untreated feed fermentation broth was determined in a similar fashion and found to result in a loading capacity of 24.8 g/l PHE. Thus, the loading capacity loss was reduced from 8.9 to 2.7 g/l PHE by the described ALAMINE 336 pretreatment, which equates to a 70% reduction in poisoning.

EXAMPLE 3

A sample of tertiary amine organic pretreatment solution (15 wt % ALAMINE 336, 18.7 wt % tridecyl alcohol, in EXXSOL D80), which had been previously contacted with a PHE fermentation broth as described in Example 2, was stripped of its loaded "poisons" by contacting 1 part with an aqueous caustic solution (1 part, 18 g/l sodium hydroxide) by continuous countercurrent extraction using a 2" diameter Karr column. The resulting stripped organic pretreatment solution was used to treat another sample of PHE fermentation broth, from the same lot as that used in Example 2, by the procedure described in Example 2. The "poison" contents of the feed broth and the pretreated broth was determined, by the procedure described in Example A, and found to result in organic loading capacities of 24.5 and 30.8 g/l PHE, respectively. This correspond to loading capacity losses of 9.2 g/l PHE for the untreated broth vs. 2.9 g/l PHE for the broth pretreated with recycled stripped organic, which equates to 69% reduction in poisoning. Thus, the effectiveness of a recycled stripped organic pretreatment solution is similar to that of a freshly prepared solution.

EXAMPLE 4

This example demonstrates a method useful for restoring the loading capacity of a quaternary organic extraction solution containing residual "poisons". A sample of "poisoned" organic extraction solution was generated by contacting an ALAMINE 336 pretreated fermentation broth (8.4 parts, 14.9 g/l PHE, pH 12) with a quaternary amine organic extraction solution (1 part).

The loading capacity of the resulting organic was determined by contacting the "poisoned" organic solution (1 part) three times with a synthetic PHE broth (2 parts, 15 g/l PHE, pH 12.0) for 60 min each, using a fresh portion of synthetic broth for the second and third contacts, and analyzing the resulting organic for PHE concentration. A loading capacity of 27.7 g/l PHE was observed. The loading capacity of the fresh quaternary amine organic extraction solution was determined in a similar fashion and found to be 34.3 g/l PHE. Thus, the "poisoning" resulted in a loss of loading capacity of 19%.

The "poisoned" organic extraction solution was contacted three times with an aqueous sulfuric acid solution (2 parts, 42.5 g/l H₂SO₄) for 30 min. each, using a fresh portion of the aqueous acid solution each time. The resulting organic was then washed with water, adding 50% sodium hydroxide to raise the pH of the separated aqueous phase to 7. The loading capacity of this acid washed organic was determined and found to be 32.2 g/l PHE. Thus, the loss of loading capacity in the organic was reduced to 6% from the loss observed prior to the described acid washing.

EXAMPLE 5

This example uses a synthetic broth to demonstrate the applicability of the process to tryptophan (TRP). Although the identity of the poisons in an actual broth is not known, a variety of acids was chosen to demonstrate the effect in principal. Approximately 30 gm l-tryptophan was dissolved in 3 l of deionized water, the pH was adjusted to 12 with 50% NaOH, and the solution was diluted to one gallon with deionized water to give solution A, analyzing at 8.1 g/l TRP. Solution A represents the control in this experiment. In 1 l of solution A was dissolved 0.5 g each of sebacic, succinic, and phenylacetic acids, and the pH was readjusted to pH 12, giving solution B, analyzing at 8.2 gl TRP. 500 ml of solution B was adjusted to pH 3 with 85% H₂SO₄ (analysis 7.7 g/l TRP) and the pretreated by contacting for 30 minutes with an equal volume of an organic phase (solution D) composed of 40 g/l Alamine 336 and 50 g/l tridecanol in Exxsol D-80 (aqueous analysis 8.0 g/l TRP). This demonstrates the selectivity of the pretreatment against TRP extraction. The pretreated broth was readjusted to pH 12 by adding 50% NaOH to give solution C (analysis 8.2 g/l TRP).

Samples of 300 ml each of aqueous solutions A, B, and C were contacted with 30 ml each of an organic solution E, composed of 45 g/l Aliquat 336 and 50 g/l tridecanol in Exxsol D-80. The separated organic phases, A1, B1 and C1 respectively, were analyzed and found to contain 13.7, 11.1 and 12.3 g/l TRP, respectively. This shows that a portion of the coextracting impurities sample B1 is eliminated by the pretreatment in sample C1.

Organic samples A1, B1, and C1 were each acid-scrubbed by washing 3 times with two volumes of 25 g/l H₂SO₄, and then washed with two volumes of 15 g/l NaOH. The maximum loading capacities of the resulting organic solutions were then determined by contacting 3 times with two volumes each of aqueous solution A. The loaded organics, A2, B2, and C2 respectively, were analyzed and found to contain 13.2, 12.9 and 13.6 g/l TRP, respectively. This demonstrates the recovery of the organic loading capacity to about the same level as the control organic.

We claim:
1. A process for the extraction of an amino acid from an aqueous solution containing same comprising
  (a) contacting said aqueous solution containing at least one amino acid at an acidic pH with a solution of a water-insoluble tertiary amine extractant in a water-immiscible organic solvent which forms a separate organic phase from said aqueous solution, said tertiary amine containing a total of at least 18 carbon atoms, said contact being maintained for a sufficient time to allow organic acid impurities present in said amino acid containing aqueous solution to be extracted from the aqueous solution phase into said organic phase while leaving said amino acid in said aqueous phase;
  (b) separation said organic phase containing said impurities from said amino acid containing aqueous phase;
  (c) contacting said amino acid containing aqueous phase at an alkaline pH with a water insoluble quaternary ammonium extractant in a water immiscible organic solvent for a time sufficient to allow the amino acids to be extracted from the aqueous phase into the quaternary ammonium extractant organic phase, said quaternary ammonium extractant containing a total of at least 16 carbon atoms;
  (d) separating the organic phase now containing said amino acids from said aqueous phase;
  (e) recovering said amino acid from said organic phase, and where any impurities remain present in said organic phase;
  (f) scrubbing said organic phase, now barren of amino acid, with an acidic scrub solution.

2. A process as defined in claim 1 wherein said amino acid is selected from the group consisting of arginine, histidine, isoleucine, leucine, lysine, methionine, β-alanine, phenylalanine, threonine, tryptophan, valine, tyrosine, glutamic acid and aspartic acid.

3. A process as defined in claim 1 wherein said amino acid is phenylalanine.

4. A process as defined in claim 1 wherein said amino acid is tryptophan.

5. A process as defined in claim 1 wherein said quaternary ammonium extractant contains a quaternary ammonium ion having the formula

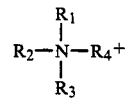

where $R_1$, $R_2$, $R_3$ and $R_4$ individually are aliphatic hydrocarbon groups containing from about 1 to 22 carbon atoms and at least three groups selected from $R_1$, $R_2$, $R_3$ and $R_4$ have at least 4 carbon atoms.

6. A process as defined in claim 5 wherein said quaternary ammonium extractant is methyltri($C_8$–$C_{10}$)ammonium chloride.

7. A process as defined in claim 1 wherein said amino acids are recovered from said quaternary ammonium organic phase by contacting said organic phase with an aqueous acidic solution whereby said amino acids are stripped from said organic phase leaving an amino acid barren, quaternary ammonium, organic phase.

8. A process as defined in claim 7 wherein said aqueous acidic solution in an aqueous sulfuric acid solution having a concentration of about 85%.

9. A process as defined in claim 7 wherein said amino acid barren, quaternary ammonium, organic phase is washed with an aqueous acidic solution.

10. A process as defined in claim 9 in which said washing with said aqueous acidic solution is carried out at an equilibrium pH of less than about 3.

11. A process as defined in claim 1 wherein prior to extraction with said tertiary amine extractant the pH of said amino acid aqueous solution is adjusted to an acidic pH below 6.

12. A process as defined in claim 11 wherein said pH is adjusted to an acidic pH in the range of about 2 to 3.5.

13. A process as defined in claim 1 wherein said tertiary amine organic phase containing said impurities is contacted with an aqueous alkaline solution whereby said tertiary amine organic phase is stripped of said impurities and regenerated for re-use.

14. A process as defined in claim 13 wherein said aqueous alkaline solution is an aqueous sodium hydroxide solution.

15. A process as defined in claim 1 wherein said tertiary amine has the formula

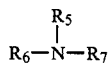

where $R_5$, $R_6$ and $R_7$ individually are aliphatic, araliphatic or aromatic hydrocarbon groups containing from 1-22 carbon with the total number of carbon atoms in groups $R_5$, $R_6$ and $R_7$ being at least 18.

16. A process as defined in claim 15 wherein said tertiary amine is methyltri($C_8$-$C_{10}$)amine.

17. A process for the extraction of phenylalanine from an aqueous solution containing phenylalanine and organic impurities comprising
  (a) contacting said aqueous solution adjusted to a pH less than 6 and containing said phenylalanine and said organic impurities with a solution of a tertiary amine dissolved in a water-immiscible organic solvent for a sufficient time to allow said impurities to be extracted from said aqueous solution and forming two immiscible phases, an organic phase (I) containing said impurities and an aqueous phase (II) containing said phenylalanine, said tertiary amine containing at least 18 carbon atoms;
  (b) separating said organic phase (I) from said aqueous phase (II);
  (c) contacting said aqueous phase (II) adjusted to a pH above 7.5 and containing said phenylalanine with a water insoluble quaternary ammonium extractant dissolved in a water-immiscible organic solvent for a time sufficient to allow said phenylalanine to be extracted from said aqueous phase (II) forming two immiscible phases, a phenylalanine containing, quaternary ammonium extractant organic phase (III) and a phenylalanine barren, aqueous phase (IV), said quaternary ammonium extractant containing at least 16 carbon atoms;
  (d) separating said organic phase (III) and said aqueous phase (IV);
  (e) recovering said phenylalanine from said organic phase (III); and
  (f) contacting said organic phase (III), now barren of phenylalanine, with an aqueous acidic solution thereby removing any remaining impurities present.

18. A process as defined in claim 17 in which said tertiary amine has the formula

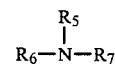

where $R_5$, $R_6$ and $R_7$ individually are aliphatic, araliphatic or aromatic hydrocarbon groups consisting from 1-22 carbon atoms with the total number of carbon atoms in groups $R_5$, $R_6$ and $R_7$ being at least 18.

19. A process as defined in claim 17 in which said quaternary ammonium extractant contains a quaternary ammonium having the formula

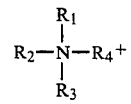

where $R_1$, $R_2$, $R_3$ and $R_4$ individually are aliphatic hydrocarbon groups containing from 1-22 carbon atoms and at least three of said $R_1$, $R_2$, $R_3$ and $R_4$ have at least 4 carbon atoms, the total number of carbon atoms in groups $R_1$, $R_2$, $R_3$ and $R_4$ being at least 16.

20. A process as defined in claim 17 in which said tertiary amine is tri($C_8$-$C_{10}$)amine and said quaternary ammonium ion is methyltri($C_8$-$C_{10}$)ammonium.

21. A process as defined in claim 17 wherein said phenylalanine is recovered from said organic phase (III) by contacting said organic phase with an aqueous sulfuric acid solution containing sulfuric acid in an amount stoichiometric to the phenylalanine present whereby said phenylalanine is stripped from said organic phase, providing a phenylalanine barren organic phase containing impurities and a phenylalanine containing aqueous phase.

22. A process as defined in claim 17 wherein said phenylalanine is recovered from said organic phase (III) by contacting said organic phase with an aqueous sulfuric acid solution having a concentration of about 85% whereby said phenylalanine is precipitated providing a phenylalanine barren organic phase containing impurities, and separating said precipitated phenylalanine from said barren organic phase.

* * * * *